(12) United States Patent
Brandon et al.

(10) Patent No.: US 7,598,082 B1
(45) Date of Patent: Oct. 6, 2009

(54) PROCESS OF MAMMALIAN CELL REPROGRAMMING THROUGH PRODUCTION OF A HETEROKARYON

(75) Inventors: Malcolm Roy Brandon, Bulleen (AU); Andrew James French, McKinnon (AU); Hongwu Chan, North Melbourne (AU); Peter Mountford, Elsternwick (AU); Megan Jayne Munsie, Hampton (AU)

(73) Assignee: Stem Cell Sciences (Australia) Pty Ltd (AU)

( * ) Notice: Subject to any disclaimer, the term of this patent is extended or adjusted under 35 U.S.C. 154(b) by 0 days.

(21) Appl. No.: 09/980,772

(22) PCT Filed: May 5, 2000

(86) PCT No.: PCT/AU00/00408

§ 371 (c)(1), (2), (4) Date: Jul. 31, 2002

(87) PCT Pub. No.: WO00/67568

PCT Pub. Date: Nov. 16, 2000

(30) Foreign Application Priority Data

| May 6, 1999 | (AU) | ................... | PQ0202 |
| May 6, 1999 | (AU) | ................... | PQ0203 |
| May 6, 1999 | (AU) | ................... | PQ0204 |
| Jun. 30, 1999 | (AU) | ................... | PQ1361 |

(51) Int. Cl.
*C12N 15/00* (2006.01)
(52) U.S. Cl. ......................... 435/373; 800/24
(58) Field of Classification Search ..................... 800/8, 800/2, 24; 435/354, 366
See application file for complete search history.

(56) References Cited

U.S. PATENT DOCUMENTS

| 5,945,577 | A | * | 8/1999 | Stice et al. ..................... 800/24 |
| 6,781,030 | B1 | * | 8/2004 | Baguisi et al. ................ 800/24 |
| 2002/0090722 | A1 | * | 7/2002 | Dominko et al. ............ 435/366 |
| 2004/0072343 | A1 | * | 4/2004 | Verma et al. ................ 435/366 |

FOREIGN PATENT DOCUMENTS

WO WO 00/67568 * 11/2000

OTHER PUBLICATIONS

Munsie et al. Reprod Fertil Dev. 1998;10(7-8):633-637 Novel method for demonstrating nuclear contribution in mouse nuclear transfer.*
Munsie et al. Curr Biol. Aug. 24, 2000;10(16):989-92. Isolation of pluripotent embryonic stem cells from reprogrammed adult mouse somatic cell nuclei.*
Thomson et al. Embryonic Cell Lines Derived from Human Blastocysts. Science. Nov. 6, 1998, vol. 282, pp. 1145-1147.*
Games et al. Alzheimer-Type Neuropathology in Transgenic Mice Overexpressing V717F Beta-Amyloid Precursor Protein. Nature. Feb. 9, 1995, vol. 373, pp. 523-527.*
Clement-Sengewald et al. Development to Term of Fused and Partially Enucleated Mouse Two-Cell Embryos. Reprod. Domestic Ani. 1990, vol. 25, pp. 14-21.*
Wakayama et al. Full-Term Development of Mice from Enucleated Oocytes Injected with Cumulus Cell Nuclei. Nature. Jul. 23, 1998, vol. 394, pp. 369-374.*
Pennisi et al. Clones: A Hard Act to Follow. Science. Jun. 9, 2000, ,vol. 288, pp. 1722-1727.*
Czolowska et al. Behaviour of Thymocyte Nuclei in Non-Activated and Activated Mouse Oocytes. J. Cell Sci., 1984, vol. 69, pp. 19-34.*
Cibelli et al. Cloned Transgenic Calves Produced From Nonquiescent Fetal Fibroblasts. Science. May 22, 1998, vol. 280, pp. 1256-1258.*
Fehilly et al. Cytogenetic and Blood Group Studies of Sheep/Goat Chimaeras. J. Reproduct. Fertility. 1985, vol. 74, pp. 215-221.*
Meirelles et al. Complete Replacement of the Mitochondrial Genotype in a Bos indicus Calf Reconstructed by Nuclear Transfer to a Bos taurus Oocyte. Genetics 2001, vol. 158, pp. 351-356.*
Mitalipov et al. Rhesus Monkey Embryos Produced by Nuclear Transfer from Embryonic Blastomeres or Somatic Cells. Biol. Reproduct. 2002, vol. 66, pp. 1367-1373.*
Simerly, C. et al. Molecular Correlates of Primate Nuclear Transfer Failures. Science. Apr. 11, 2003, vol. 300, p. 297.*
Campbell. Nuclear Equivalence, Nuclear Transfer and the Cell Cycle. Cloning. 1999, vol. 1, pp. 3-15.*
Matveeva et al. In Vitro and In Vivo Study of Pluripotency in Intraspecific Hybrid Cells Obtained by Fusion of Murine Embryonic Stem Cells with Splenocytes. Molec. Reprod. Devel. 1998, vol. 50, pp. 128-138.*
Tada et al. Embryonic Germ Cells Induce Epigenetic Reprogramming of Somatic Nucleus in Hybrid Cells. EMBO J. 1997, col. 16, pp. 6510-6520.*
Rousset et al. Hybrids Between F9 Nullipotent Teratocarcinoma and Thymus Cells Produce Multidifferentiated Tumors in Mice. Develop. Biol. 96, pp. 331-336.*
Gasaryan, et al.: Nuclear transplantation in teleost *Misugmus fossolis* L.; Nature, vol. 280, Aug. 16, 1979, pp. 585-587.
Niwa, Katsutoshi, et al., Transplantation of blastula nuclei to non-nucleated eggs in the medaka, *Oryzias latices*, Develop. Growth Differ. (1999) 41, 163-172.
Thomson JA,Itskovitz-Eldor J. Shapiro 55. Waknitz MA,Swlerglei JJ. Marshall VS. Jones JM: Embryonic stem cell lines derived from human blastocysts. Science 1998.282:1145-1147.
Reubinoff BE. Pera MF. Fong CY. Trounson AO. Bongso A: Embryonic stem cell lines from humanblastocysts: somatic differentiation In vitro. Nature Biotechnology 2000,18: 399-404.
Smith AG : Cell therapy: In search of pluripotency. Current Biology 1998.8: R802-804.
Solter O: Dolly is a clone-and no longer alone. Nature 1998,394: 315.

(Continued)

*Primary Examiner*—Deborah Crouch
(74) *Attorney, Agent, or Firm*—Tucker Ellis & West LLP

(57) ABSTRACT

This invention relates to the reprogramming of animal cells and animal cell nuclei by nuclear addition. The invention also relates to the generation of animal cells, cell lines, tissues, organs, embryos and non-human animals by methods involving nuclear addition.

20 Claims, 3 Drawing Sheets

OTHER PUBLICATIONS

Figure 1:
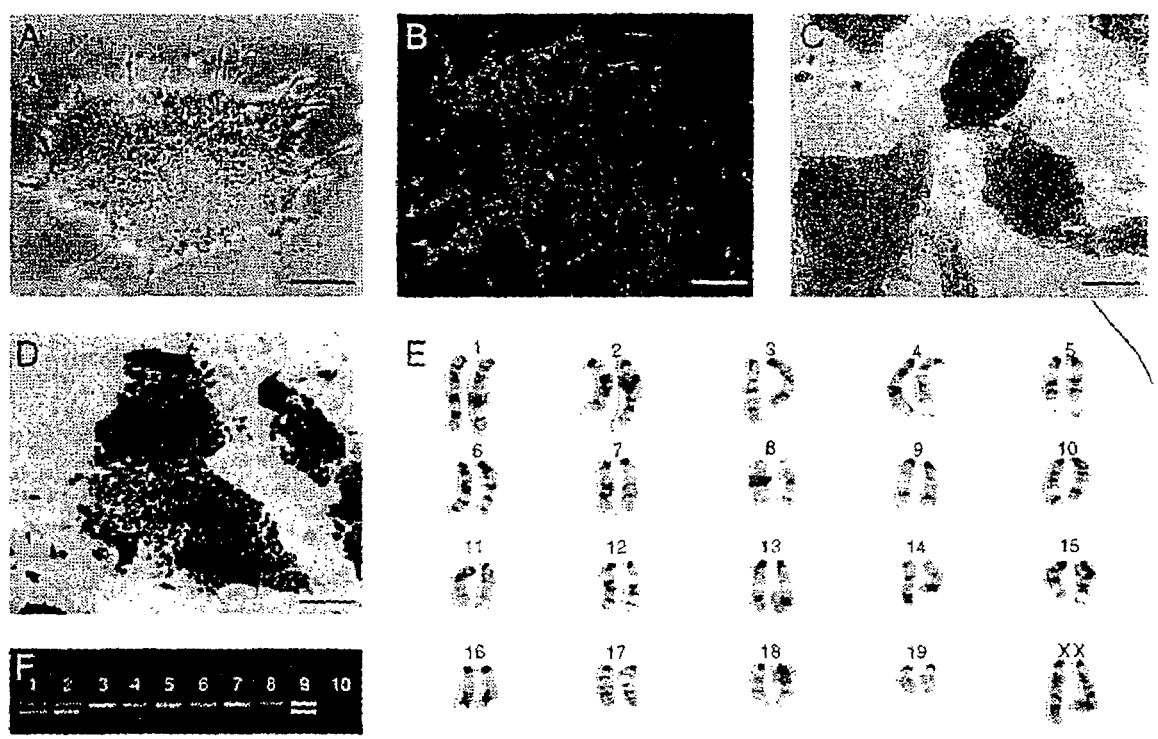

Wilmut I. Schnieke AE. McWhir J. Kind AJ.Campbell KH: Viable offspring derived from fetal and adult mammalian cells. Nature 1997,385: 810-813.

Wakayama T. Perry AC. Zuccotti M. Johnson KR. Yanagimachi R: Full-term development of mice from enucleated oocytes injected with cumulus cell nuclei. Nature 1998.394: 369-374.

Mountford PM. Smith AG: Internal ribosome entry sites and dicistronic RNAs inmammalian transgenesis.TIG 1995.11: 179-184.

Munsie M. Peura TP, MichalskaA. Trounson AD. Mountford PS: Novel method for demonstrating nuclear contribution in mouse nuclear transfer. Reproduction Fertility and Development 1998.10: 633-637.

Cibelli JB. Stice SL. Golueke PJ. Kane JJ. Jerry J, Blackwell C. Ponce de Leon FA.Robl JM: Transgenic bovine chimeric offspring produced from somatic cell-derived stem-like cells. Nature Biotechnology 1998.16: 642-646.

Klug MG. Soonpaa MH. Koh GY.Field LI: Genetically selected cardiomyocytes from differentiating embronic stem cells form stable intracardiac grafts. Journal of Clinical Investigation 1996.98: 216-224.

McDonald JW. Liu X-Z, Qu Y, Liu S.Mickey SK. Turetsky D.Gottlieb DI. Choi DW: Transplanted embryonic stem cells survive, differentiate and promote recovery in injured ratspinal cord. Nature Medicine 1999.5:1411412.

Potocnik AJ. Kohler H. Eichmann K: Hemato-lymphoid in vivo reconstitution potential of subpopulations derived from in vitro differentiated embryonic stem cells. Proc Natl Acad Sci USA 1997.94: 10295-10300.

Soria B. Roche E. Berna G, Leon-Qulnto T. Reig JA. Matrin F:Insulin-sectreting cells derived from embryonic stem cells normalize glycemla in streptozotocin-induced diabetic mice. Diabetes 2000. 49:157-162.

Barnes FL. Cromble A. Gardner OK. Kausche A.Lacham-Kaplan O, Suikkari A-M. Tigilas J. Wood C. Trounson AO. Blastocyst development and birth after In vitro maturation of human primary oocytes. Intracytoplasmic sperm injection and assisted hatching. Hum Reprod1995,10: 3243-3247.

Robertson EJ: Teratocarcinomas and embryonic stem cells: A practical Approach. Oxford: IRL Press: 1987.

Smith AG: Culture and differentiation of embryonic stem cells. J Tiss Cult Meth 1991.13: 89-94.

Buehr M. McLaren A: Isolation and culture of primordial germ cells. MethodsEnzymol 1993.225: 58-77.

van Eijk MJT, van Rooljen MA, Modina S, Scesi L, Folkers G, van Tol HTA, Bevers MM, Fisher SR, Lewin HA, Rakacolli D, Galli C, de Vaureix C. Trounson AD. Mummery CL, Gandolfi F: Molecular cloning, genetic mapping, and developmental expression of bovinePOUSFI. Biol Reprod 1999.60:1093-1103.

Agulnik AI. Longepied G. Ty MT, Bishop CE. Mitchell M: Mouse H-Y encoding Smcy gene and its Xchromosomal homolog Smcx. Mamm Genome 1999.10:925-929.

Nagy A. Rossant J. Nagy R. Abramow-Newerly W. Roder JC: Derivation of completely cell culture-derived mice from early-passage embryonic stem cells. ProcNatl Acad Sci USA1993.90: 8424-8428.

Bradley A: Teratocarcinomas and embryonic stem cells: A practical approach. Oxford: IRL Press: 1987.

U M. Pevny L. Lovell-Badge R. Smith A: Generation of purified neural precursors from embryonic stem cellsby lineage selection. Curr Biol 1998. 8: 971-974.

Ooetschman TC.Elstetter H, Katz M. Schmidt W. Kemler R: The in vitro development of blastocyst-derived embryonic stem cell lines: formation of visceralyolk sac, blood islands and myocardium. J Embryol Exp Morphol 1985.87:27-45.

Beddington RSP, Morgenstern J, Land H. Hogan A. An in situ transgenic enzyme marker for the midgestatlon mouse embryo and the visualization of innercell mass clones during early embryogenesis. Development 1989.106:37-46.

Sambrook. J.. Fritsch. E. F., Maniatis. T., [1989]Molecular Cloning-A Laboratory Manual, Cold Spring Harbour Laboratory Press. New York1: 26 [O'Gorman. S.. Fox. D. T.,Wahl, G. M. [1991] Recombinase-mediated gene activation and site-specific integration in mammaliancells. Science 251 [4999].1351-5].

O'Gorman. S., Fox. O.T.. Wahl, G.M. [1991] Recombinase-mediated Gene Activation and Site-specific Integration in Mammalian Cells. Science 251 [4999].1351-5.

* cited by examiner

SEQUENCE LISTING

<160> NUMBER OF SEQ ID NOS: 8

<210> SEQ ID NO 1
<211> LENGTH: 21
<212> TYPE: DNA
<213> ORGANISM: Artificial
<220> FEATURE:
<223> OTHER INFORMATION: Synthetic construct

<400> SEQUENCE: 1
gttctctttg gaaaggtgtt c                                                   21

<210> SEQ ID NO 2
<211> LENGTH: 20
<212> TYPE: DNA
<213> ORGANISM: Artificial
<220> FEATURE:
<223> OTHER INFORMATION: Synthetic

<400> SEQUENCE: 2
actcgaacca catccttctc                                                     20

<210> SEQ ID NO 3
<211> LENGTH: 20
<212> TYPE: DNA
<213> ORGANISM: Artificial
<220> FEATURE:
<223> OTHER INFORMATION: Synthetic construct

<400> SEQUENCE: 3
gttgcagggt aaccgatgaa                                                     20

```
<210> SEQ ID NO 4
<211> LENGTH: 20
<212> TYPE: DNA
<213> ORGANISM: Artificial
<220> FEATURE:
<223> OTHER INFORMATION: Synthetic construct

<400> SEQUENCE: 4
tgttgtgggt atgctggtgt                                               20

<210> SEQ ID NO 5
<211> LENGTH: 18
<212> TYPE: DNA
<213> ORGANISM: Artificial
<220> FEATURE:
<223> OTHER INFORMATION: Synthetic construct

<400> SEQUENCE: 5
tgaagctttg gctttgag                                                 18

<210> SEQ ID NO 6
<211> LENGTH: 19
<212> TYPE: DNA
<213> ORGANISM: Artificial
<220> FEATURE:
<223> OTHER INFORMATION: Synthetic construct

<400> SEQUENCE: 6
ccgctgccaa attctttgg                                                19

<210> SEQ ID NO 7
<211> LENGTH: 20
<212> TYPE: DNA
<213> ORGANISM: Artificial
<220> FEATURE:
<223> OTHER INFORMATION: Synthetic construct

<400> SEQUENCE: 7
actatcccga ccgccttact                                               20

<210> SEQ ID NO 8
<211> LENGTH: 20
<212> TYPE: DNA
<213> ORGANISM: Artificial
<220> FEATURE:
<223> OTHER INFORMATION: Synthetic construct

<400> SEQUENCE: 8
tagcggctga tgttgaactg                                               20
```

PROCESS OF MAMMALIAN CELL REPROGRAMMING THROUGH PRODUCTION OF A HETEROKARYON

This invention relates to the reprogramming of animal cells and animal cell nuclei by nuclear addition. The invention also relates to the generation of animal cells, cell lines, tissues, organs, embryos and non-human animals by methods involving nuclear addition.

Nuclear addition is the addition of the nucleus of one cell to that of another. Nuclear addition differs from nuclear transfer in that a nucleus is added to a non-enucleated cell which may then lose or be subjected to a subsequent removal (enucleation) of the recipient or host cell's nucleus or nuclear DNA. Nuclear addition has certain advantages over nuclear transfer which can enhance the efficiency of nuclear reprogramming and developmental competence for the generation of animal cells, cell lines, tissues, organs, embryos and animals for agricultural, medical, veterinary and research applications.

Nuclear transfer has been used to generate cloned offspring by transferring a donor nucleus into an oocyte from which the maternal chromosomes have first been removed or enucleated.

The ability to produce cloned offspring, for example by nuclear transfer, enables the production of large numbers of identical offspring and the opportunity to select for the desired animal genotype. For example, nuclear donor cell sources may be selected from animals, embryos, cultured cells or cultured cell lines on the basis of patient specific or donor matching of major histocompatibility genes, or animal gender, disease resistance, enhanced productivity traits or for any other reason. Similarly, nuclear donor cells may be selected from genetically engineered or modified cells for the production of transgenic cells, embryos and non-human animals.

Whilst cell reprogramming via nuclear transfer has been described in some animals, the procedures used are often inefficient.

It is an object of the present invention to overcome, or at least alleviate, one or more of the difficulties or deficiencies associated with the prior art.

In a first aspect of the present invention there is provided a method of preparing a reprogrammed diploid cell which method includes
 providing
  a donor cell or donor nucleus, and
  a recipient cell;
 introducing the donor cell or donor nucleus into the recipient cell to produce an aneuploid cell;
 maintaining the aneuploid cell in a suitable environment for a period sufficient to allow the donor nucleus to be reprogrammed; and
 generating a reprogrammed diploid cell from said reprogrammed aneuploid cell by removal, destruction or loss of the recipient cell nucleus or nuclear DNA from said reprogrammed aneuploid cell.

Applicant has found that nuclear addition is potentially less disruptive than nuclear transfer. In nuclear addition, the donor nucleus is placed into an intact cell and is exposed to reprogramming factors. These reprogramming factors may be associated with the metaphase plate, cell nucleus, chromatin, chromosomes or DNA, or with the cytoplasmic components of the recipient cell which would normally be removed or depleted through nuclear transfer procedures. Nuclear addition allows the donor nucleus to be exposed to these factors with minimal disruption to cell function.

Nuclear addition involves the subsequent loss, destruction or removal (enucleation) of the recipient cell's metaphase plate, nucleus, chromatin, chromosomes or DNA following or simultaneously with the introduction of the donor nucleus. The length of time the donor cell is exposed to the reprogramming factors may be influenced by the process of enucleation. An aneuploid cell is produced when the donor nucleus is introduced to the recipient cell. An aneuploid cell for the purposes of this document includes polypoid cells. The cell remains an aneuploid cell if the cell's metaphase plate, nucleus, chromatin, chromosomes or nuclear DNA is not lost, removed or destroyed following nuclear addition of the donor cell's nucleus. A reconstituted diploid cell is a cell where subsequent to or simultaneously with nuclear addition, the recipient cell's metaphase plate, nucleus, pronucleus, chromatin, chromosomes or nuclear DNA is lost from the cell, removed from the cell or destroyed.

The methods of the present invention may be used to generate cells which are reprogrammed, for example at least partially reprogrammed (e.g. de-differentiated) to an alternate somatic cell state, or substantially fully reprogrammed (eg. de-differentiated) to an embryonic cell fate. For example, a gene or genes associated with the reprogrammed state may be activated and/or a gene or genes expressed in the donor cell may be repressed in the reprogrammed cell.

The method of the present invention may be used to reprogram cells which have been genetically engineered. Nuclear donor cells may be selected from genetically engineered or modified cells for the production of genetically engineered stem cells, stem cell lines and stem cell-derived cells or cell lines, for example, pluripotent embryonic stem (ES) cells or ES-derived somatic cells which may be isolated, purified or propagated by the method known as stem cell selection.

Accordingly, in a second aspect of the present invention there is provided a method of preparing a reprogrammed genetically modified diploid cell, said method including
 providing
  a donor cell or donor nucleus which donor cell or nucleus has been genetically modified to eliminate or reduce an undesirable activity or to provide for or increase a desirable activity, and
  a recipient cell;
 introducing the donor cell or nucleus into the recipient cell to produce an aneuploid cell;
 maintaining the aneuploid cell in a suitable environment for a period sufficient to allow the donor nucleus to be reprogrammed; and
 generating a reprogrammed genetically modified diploid cell from said reprogrammed aneuploid cell by removal, destruction or loss of the recipient cell nucleus or nuclear DNA from said reprogrammed aneuploid cell.

In a third aspect of the present invention there is provided a method of preparing a reprogrammed genetically abnormal cell, said method including
 providing
  a donor cell or donor nucleus which donor cell or nucleus is derived from a genetically abnormal cell, such as a cell from an animal or person with a genetic disease, and
  a recipient cell;
 introducing the donor cell or nucleus into the recipient cell to produce an aneuploid cell;
 maintaining the aneuploid cell in a suitable environment for a period sufficient to allow the donor nucleus to be reprogrammed; and
 generating a reprogrammed genetically abnormal cell with an equivalent genetic composition to the said abnormal donor cell nucleus from said reprogrammed aneuploid cell by removal, destruction or loss of the recipient cell nucleus or nuclear DNA from said reprogrammed aneupliod cell.

The reprogrammed cells may be used in basic and applied research, cell-based gene and drug screening, diagnostics, and/or cell-based gene and tissue therapies. More particularly, reprogrammed abnormal cells may be used in cell-based gene and drug screening for the discovery and/or development of new therapeutic and prophylactic treatments for characterised and uncharacterised single gene and multigenic diseases.

The donor nucleus may be of any suitable type and from any suitable species. The donor nucleus may be contained in a karyoplast or cell. The donor nucleus may be of embryonic, foetal, new born, juvenile or adult origin. Donor nuclei may be prepared by removing the nucleus and a portion of the cytoplasm and plasma membrane surrounding the donor nucleus from a suitable donor cell for example using microsurgery. Adult cells such as fibroblasts, cumulus cells, lymphocytes and neural cell types may be used. In a preferred embodiment, the donor nucleus may be from a somatic cell, more preferably an adult somatic cell, or a somatic stem cell. Cell lines may be used. In a particularly preferred embodiment embryonic cells such as embryonic stem cells or other pluripotent stem cell lines, embryonic germ cells or primordial germ cells may be used.

It is particularly preferred that the donor cells be at a particular stage in the cell cycle, for example $G_0$, $G_1$ or S-phase. Applicant has found that it is possible to isolate populations of cells which are enriched for cells at each stage in the cell cycle by sorting the cells on the basis of size, for example using FACS. This avoids the use of stains, which may be toxic to the cells. Staining can be used on a sample of each size-sorted population to identify what stage in the cell cycle that population is at.

The donor nucleus may be from a normal, abnormal or from genetically modified cell. Donor nuclei may be isolated directly from an animal cell, from an animal cell culture or from an established cell line. Abnormal cells include cells with known or unknown genetic mutations including gene and other chromosomal mutations, deletions, rearrangements, substitutions and/or duplications.

The recipient cell may be of any suitable type and from any suitable species. The recipient cell may be an in vivo or in vitro produced oocyte. Oocytes may be, for example, germinal vesicle (GV) stage or metaphase I (MI) immature oocytes, or oocytes arrested in the second metaphase of meiotic maturation (MII oocytes). Other sources of recipient cells include zygotes, fertilised oocytes, embryonic blastomeres (e.g. 2-cell blastomeres) and cell lines produced from gonads, germ cell tumours or any other cell type suitable for allowing the successful addition of a nucleus. In addition, the recipient cell may be a pluripotent cell such as an embryonic stem (ES) cell, embryonic germ cell or primordial germ cell [which includes cells isolated from cell lines, primary cultures or isolated cells from the inner cell mass (ICM), embryonic disc (ED), embryonic ectoderm or primordial germ cells (PGCs)], a cell derived from a tumor including an embryonal tumor may be used (eg. embryonal carcinoma (EC) or yolk sac tumor cells). Somatic cell recipients such as neural or haematopoietic stem cells may be used as a source of recipient cell. Oocytes, for example arrested in the second metaphase of meiotic maturation (MII oocytes) are preferred.

The donor nucleus (or nuclei) or cell(s) may be transferred to the recipient cell by any suitable method. Such methods include, but are not limited to, microsurgical injection, and cell fusion for example mediated by electrical pulses (electrofusion), chemical reagents such as polyethyleneglycol, or the use of inactivated virus such as Sendai virus.

Preferably the donor nucleus is introduced, for example under the zona pellucida, by microsurgery.

In a particularly preferred embodiment the donor nucleus or cell may be transferred to the recipient cell by piezo-assisted micromanipulation.

In a preferred form of these aspects of the invention, the recipient cell may be subject to a pre-treatment step, although this step is optional. More particularly, the metaphase plate, nucleus, chromatin, pronucleus chromosomes or nuclear DNA of the recipient cell may be subjected to a pre-treatment step.

Pretreatment of the recipient cell/s may include incubation of the cell/s in a microfilament inhibitor, for example cytochalasin B that relaxes the cytoskeleton and facilitates the removal of a portion of membrane enclosed cytoplasm containing the recipient cell's pronuclei, metaphase plate, nucleus, chromosomes or DNA, concomitant with or preferably after a period of time following the introduction of the donor nucleus. Chemical treatments such as, but not limited to, one or a combination of taxol, etoposide demecolcine and cycloheximide may be used to assist in the disablement or expulsion of the recipient cell's metaphase plate, nucleus, pronucleus, chromatin, chromosomes or DNA from the cell concomitant with or preferably after a period of time following the introduction of the donor nucleus. Alternatively, non-chemical approaches may be used to assist in the disablement or expulsion of the recipient cell's metaphase plate, nucleus, chromatin, chromosomes or DNA from the cell which includes, but are not limited to, inactivation, disablement, damage or destruction of the metaphase plate, pronucleus, nucleus, chromatin, chromosomes and/or DNA by ultraviolet light (UV), laser or other forms of irradiation.

Pre-Treatment May Also Include Activation.

Activation occurs during fertilisation when the penetrating sperm triggers the resumption of meiosis. Activation is characterised by calcium oscillation, release of cortical granules, extrusion of the second polar body, pronuclear formation and ultimately cleavage. The recipient or aneuploid cell may be treated with, but not limited to, for example, ethanol, calcium ionophore or electrical stimulation to induce activation. Activation may be performed prior to, concomitant with, or after the transfer of the donor nucleus.

A preliminary activation step may be undertaken prior to transfer of the donor nucleus and may affect the reprogramming factors associated with the recipient cell's nucleus, pronucleus, metaphase plate, chromatin, chromosomes or DNA.

Pre-treatment may also include the disablement or destruction of the recipient cell's nucleus, pronucleus, metaphase plate, chromatin, chromosomes or DNA which may reduce or eliminate co-mingling of the recipient cell's nucleus, pronucleus, metaphase plate, chromatin, chromosomes or DNA with that of the donor. Embryos so formed may not be clones, and may, in turn, not develop to full-term.

The step of generating a reprogrammed diploid cell from said reprogrammed aneuploid cell may be performed by any suitable method. For example, the aneuploid cell may be maintained in a suitable environment for a period sufficient for the aneuploid cell to generate a diploid cell through loss of the recipient cell's metaphase plate, nucleus, pronucleus, chromatin, chromosomes or DNA from the aneuploid cell, or, the disproportionate distribution of the aneuploid cell's metaphase plate, nucleus, chromatin, chromosomes or DNA in the daughter cells of the aneuploid cell. Alternatively, the diploid cell may be generated by the removal of the recipient cell's metaphase plate, nucleus, pronucleus, chromatin, chromosomes or DNA from the aneuploid cell or a daughter cell of the aneuploid cell, or destruction of the recipient cell's metaphase plate, nucleus, pronucleus, chromatin, chromosomes or DNA in the aneuploid cell or a daughter cell of the aneuploid cell.

In one form of these aspects of the present invention, the methods may include the further step of substantially removing or substantially destroying the nucleus, pronucleus, metaphase plate, chromatin, chromosomes or DNA of the recipient cell, preferably prior to division of the aneuploid cell.

Removal or destruction of the nucleus, pronucleus, metaphase place, chromatin, chromosomes or DNA of the recipient cell may be performed, for example, approximately 1 to 20, more preferably approximately 3 to 12, most preferably approximately 6 to 8 hours after completion of the nuclear addition procedure, and prior to first embryo cleavage. Destruction of the DNA may be achieved utilising chemical or laser or other radiation-based microsurgical techniques or the like.

Removal or destruction of the recipient cell's nucleus, pronucleus, metaphase plate, chromatin, chromosomes or DNA may occur spontaneously through a developmental self-correction mechanism(s) which would restore ploidy to some if not all cells.

Loss or removal of the recipient cell's metaphase plate, nucleus, chromatin, chromosomes or DNA may be assessed by the use DNA chelating agent such, as but not limited to, Hoechst 33342 and UV illumination, or the use of Pol-Scope imaging to visualise the recipient cell's metaphase plate, pronucleus, nucleus, chromatin or chromosomes.

In another form of these aspects of the invention, the methods may include the further steps of providing a co-mingling inhibitor, and subjecting the aneuploid cell to a co-mingling inhibitor for a period sufficient to reduce or eliminate co-mingling of the recipient cell DNA and introduced DNA.

The co-mingling inhibitor may be a cytoskeletal (cytokinesis) or karyokinesis inhibitor, for example, but not limited to, those selected from the group consisting of one or more of Cytochalasin B, Colcemid, Taxol or Nocodazole. The aneuploid cell may be exposed to the co-mingling inhibitor for a period, up to pronuclear formation, of for example approximately 1 to 6 hours after nuclear addition and preferably prior to embryo cleavage.

In another form of these aspects of the invention, the recipient cell may be enucleated substantially simultaneously with introduction of the donor cell or nucleus. Preferably the donor nucleus is introduced into the enucleated cell substantially immediately before enucleation. More preferably the donor nucleus is introduced into the enucleated cell via an incision site and the recipient nucleus is removed from the cell through the same incision site.

The methods of the present invention, may include the further step of subjecting the recipient cell, the aneuploid cell or the diploid cell to an activation step.

The recipient, aneuploid or diploid cell may be treated with, but not limited to, for example, ethanol, calcium ionophore or electrical stimulation to induce activation. Activation may be performed prior to, concomitant with, or after the transfer of the donor nucleus.

As discussed earlier, a preliminary activation step may be undertaken prior to transfer of the donor nucleus or the juxtaposed donor and recipient cells may be subjected to a cell fusion/activation step. For example, where electrical pulses are utilised for cell fusion, the voltage may be selected to simultaneously initiate activation.

The juxtaposed donor and recipient cells may be also subjected to simultaneous cell fusion/activation or a process of cell fusion followed later by activation.

The aneuploid cell is maintained in a suitable environment for a time sufficient to allow the donor nucleus or cell to be reprogrammed. Preferably, the aneuploid cell is maintained in a suitable environment for a period of approximately 1 to 36 hours, more preferably approximately 1 to 8 hours. The aneuploid cell may be maintained in a suitable culture medium in vitro, or transferred to a surrogate animal and maintained in vivo.

The donor nucleus and recipient cell which are used in the method of the present invention may be of any suitable origin and need not be from the same species. Species to which the present invention may be applied include birds, fish, reptiles and mammals (including ungulates and primates). Preferably, the cells are of porcine, bovine, ovine, rodent, avian, fish, reptile, murine or human origin.

In a preferred embodiment, the methods of the present invention may include the further steps of removing the donor nucleus from the aneuploid cell; and introducing said removed donor nucleus into a second recipient cell (enucleated or non-enucleated) to produce a reprogrammed second cell, a genetically modified reprogrammed second cell or a genetically abnormal reprogrammed second cell.

In a preferred embodiment of the methods of the present invention, the removed donor nucleus may be from an embryo that is itself the product of nuclear addition or nuclear transfer. The former is known as serial nuclear addition.

Serial nuclear addition or a combination of nuclear addition and nuclear transfer may improve the capacity of differentiated nuclei to direct normal development. Whilst applicant does not wish to be restricted by theory, serial nuclear addition and/or transfer is postulated to improve the developmental capacity of transplanted nuclei by allowing specific molecular components in the oocyte to assist in chromatin remodelling that is beneficial for nuclear reprogramming. Serial nuclear addition or a combination of nuclear addition and nuclear transfer is not restricted to a singular event but may be initiated on more than one occasion to sequentially improve conditions for chromatin remodelling, nuclear reprogramming and embryonic development.

The donor nucleus may be genetically modified by modifying, deleting or adding one or more genes. The gene(s) to be modified, deleted or added may be of any suitable type.

The process of modifying, adding or deleting a gene may involve random or targeted integration of a transgene. Transgenes may be fully functional genes or expression constructs comprised of heterologous gene sequences including enhancers, repressors, promoters, exons, introns, cDNAs, coding sequences, antisense RNA, 5' or 3' non-coding regions and other RNA processing signals or elements including translational start and stop signals, internal ribosome entry sites (IRESs) and polyadenylation signals. Transgenes may be non-functional components of a gene or heterologous components of different genes which are dependent upon integration (random or targeted) into the host genome. Such transgenes include gene traps, promoter traps, enhancer traps and other DNA constructs harbouring point mutations or otherwise capable of modifying expression of an endogenous gene.

The process of modifying a gene may involve the introduction of one or more mutations in both copies of the target gene. Suitable cells may take up the mutation(s) and then be used to generate a reprogrammed cell, cell line, embryo or non-human animal. One copy of the gene may be disrupted in the cell and the resultant heterozygous non-human animals bred with each other until an animal with both copies of the gene mutated is obtained. Alternatively, both copies of the gene may be modified in vitro.

To target an endogenous gene rather than introduce transgenes into random locations in the genome, a DNA construct (transgene) including a nucleic acid sequence which is in part substantially isogenic to at least one or more portions of the target gene may be used.

The targeting DNA may comprise a sequence in which the desired sequence modifications are flanked by DNA substantially isogenic with a corresponding target sequence in the genome to be modified. The substantially isogenic sequence is preferably at least about 97-98% identical with the corresponding target sequence (except for the desired sequence modifications), more preferably at least about 99.0-99.5% identical, most preferably about 99.6% to 99.9% identical. The targeting DNA and the target DNA preferably share stretches of DNA at least about 75 base pairs that are perfectly identical, more preferably at least about 150 base pairs that are perfectly identical, even more preferably at least about 500 base pairs that are perfectly identical. Accordingly, it is preferable to use targeting DNA derived from cells as closely related as possible to the cell being targeted; more preferably, the targeting DNA is derived from cells of the same genotype as the cells being targeted. Most preferably, the targeting DNA is derived from cells of the same individual (or animal) as the cells being targeted. Preferably, the targeting DNA sequence comprises at least about 100-200 base pairs of substantially isogenic DNA, more preferably at least about 300-1000 base pairs of substantially isogenic DNA, even more preferably at least 1000-15000 base pairs of substantially isogenic DNA.

As used herein, the term isogenic or substantially isogenic DNA refers to DNA having a sequence that is identical with or nearly identical with a reference DNA sequence. Indication that two sequences are isogenic is that they will hybridise with each other under the most stringent hybridisation conditions (see, for example, reference 25) and will not exhibit sequence polymorphism (i.e. they will not have different sites for cleavage by restriction endonucleases). The term "substantially isogenic" refers to DNA that is at least about 97-99% identical with the reference DNA sequence, and preferably at least about 99.5-99.9% identical with the reference DNA sequence and in certain cases 100% identical with the reference DNA sequence. Indications that two sequences are substantially isogenic is that they will still hybridise with each other under the most stringent conditions (25) and that they will only rarely exhibit restriction fragment length polymorphism (RFLP) or sequence polymorphism (relative to the number that would be statistically expected for sequences of their particular length which share at least about 97-98% sequence identity). In general, a targeting DNA sequence and a host cell sequence are compared over a window of at least about 75 consecutive nucleotides. DNA sequences compared between individuals of a highly inbred strain are generally considered to be substantially isogenic even if detailed DNA sequence information is not available, if the sequence do not exhibit sequence polymorphisms by RFLP analysis.

Thus, the donor nucleus may be genetically modified by modifying an endogenous gene in the donor nucleus. The endogenous gene may be modified by introducing into said donor nucleus a DNA construct including a nucleic acid sequence which is substantially isogenic to at least one or more portions of the endogenous gene and includes one or more mutations or new gene sequences, such that there is homologous recombination between the DNA construct and the endogenous gene.

The introduction of new genetic material and the subsequent selection of cells harbouring the desired targeted integration requires expansion and clonal selection of each founder transgenic cell. A limitation to applying this process in nuclear transplantation programs is the number of cell divisions which the transfected cell must undergo to provide sufficient material for molecular analysis of each transgenic colony and subsequent supply of nuclei for transfer. The great majority of cells suitable for in vitro genetic modification and subsequent nuclear transfer have limited in vitro propagation capacity. It is therefore desirable to utilise transfection and selection systems which generate and/or identify correctly targeted clones at high efficiency and with limited requirement for in vitro propagation.

A particularly efficient approach to selecting for correctly targeted clones is to use IRES gene trap targeting vectors, as described in Australian Patent 678234, the entire disclosure of which is incorporated herein by reference. The IRES gene trap targeting vector may be selected from IRES-neo, IRES-lacZ, $(TAA_3)$ IRES-lacZ, $(TAA_3)$ IRES-lacZ lox neo-tk lox, $(TAG_3)$ IRES-lacZ/mcineo, SA lacZ-IRES neo, SA $(TAA_3)$ IRES-nuclear lacZ, SA $(TAA_3)$ IRES-nuclear lacZ lox Gprt lox, IRES-B-geo, $(TAA_3)$ IRES-B-geo, SA IRES-B-geo SA Optimised IRES-B-geo, IRES-nuclear B-geo, SA IRES-nuclear B-geo, SA $(TAA_3)$ IRES-nuclear B-geo, SA Optimised IRES-nuclear B-geo, IRES-zeo, SA IRES-zeo, IRES-hph, SA IRES-hph, IRES-hph-tk, IRES-bsd, SA IRES-bsd, IRES-puro. IRES gene trap targeting vectors provide a significant enhancement in gene targeting efficiency by eliminating a large proportion of random integration events. IRES gene trap targeting vectors rely upon functional integration into an actively transcribed gene (such as the target gene) for expression of the selectable marker. Random integrations into non-transcribed regions of the genome are not selected.

In a preferred embodiment, it may be desirable to remove the selectable marker cassette from the targeted locus to eliminate expression of the eg. antibiotic resistance gene. One approach is to flank the IRES selectable marker cassette with suitable DNA sequences which act as recombination sites following the addition of a suitable site-specific recombinase. One example of a suitable recombinase site is the lox site which is specific for the Cre recombinase protein. Another example of a suitable recombinase is the FLP/FRT recombinase system (26).

High efficiency gene targeting and selection has a significant advantage in that suitably stringent selection systems, such as the IRES gene trap targeting vectors, can eliminate the need for biochemical analysis of clonal cell lines. In this instance, individual nuclei from a pool of uncharacterised transgenic cells should generate offspring of the desired phenotype at a ratio equivalent to the selected pool. The elimination of clonal selection may be particularly useful where only limited in vitro propagation is desirable or possible. One such instance includes the culture of embryonic nuclei for nuclear addition or nuclear transfer. Embryonic nuclei are more efficient than latter stage somatic cells for generating live born offspring by nuclear transfer. However, totipotential embryonic cells can not be cultured for extended periods for any other species than mice and potentially primates including man. Nuclear recycling through serial nuclear addition of embryonic nuclei provides an opportunity to maintain, expand and genetically manipulate multipotential cells from animals in vitro.

The DNA constructs may be engineered in bacteria and then introduced into the cells. The transgenes may be introduced into the cells by any suitable method. Preferred methods include direct injection, electroporation, liposomes or calcium phosphate precipitation.

Whilst applicant does not wish to be restricted by theory, it is thought that regions of substantially isogenic DNA either side of the mutation preferentially align the transgene with the target site where it recombines and introduces the mutation. It is further thought that the main contributing factor for increasing the efficiency of introducing a specific mutation in a given gene is the degree of similarity between the target DNA and the introduced DNA. Thus, it is preferred that the DNA is isogenic (genetically identical) not allogenic (genetically dissimilar) at the genetic locus that is to be targeted.

As used in this specification the term "transgenic" should not be taken to be limited to referring to cells containing one or more genes from another species, although many transgenic cells will contain such a gene or genes or fragments thereof. Rather, the term refers more broadly to any cell whose DNA has been the subject of technical intervention by recombinant DNA technology. So, for example, a cell in which an endogenous gene has been deleted or modified (either by modifying the gene product or pattern of expression) is a transgenic cell for the purposes of this invention, as much as a cell to whose DNA an exogenous nucleic acid sequence has been added.

Reprogrammed cells according to the present invention may be used to generate cells, cell lines, tissues, organs, animal embryos and non-human animals. These products may be derived from reprogrammed embryonic cells (where the recipient cell is an oocyte or other embryonic cell such as an embryonic stem cell or primordial germ cell) or reprogrammed somatic cells (where a recipient cell is specific somatic cell type such as a liver or neural stem cell) and may be used to restore function to tissue that has been damaged by injury, disease or aging. Transferred cells may also be used to re-populate a depleted tissue or be genetically altered prior to transplantation to deliver gene therapy.

Cells and cell lines derived from reprogrammed cells or embryos may also be used in cell-based gene and drug screening and diagnostic assays to assess for the presence or absence, function, efficacy, toxicity or any other biological property of a gene, gene product or other biologically active compound. Cells, cell lines, tissues and organs derived from reprogrammed cells may be used for medical, veterinary, agricultural applications and/or basic research. Tissues or organs derived from reprogrammed cells, or from animals or embryos that have developed from reprogrammed embryos, may also be used to treat patients with diseased or defective cells, tissues or organs. Cells, cell lines, embryo-derived cell lines, tissues and organs may be established using a patients own cells as a donor source and would therefore avoid possible tissue rejection following transplantation.

Accordingly, the methods of the present invention may include the further step of generating cells, cell lines, tissues, organs, animal embryos or non-human animals from said reprogrammed cells or from cells reprogrammed by serial nuclear addition with or without nuclear transfer.

The method of the present invention may also include the further step of generating genetically modified or genetically abnormal cells, cell lines, tissues, organs, animal embryos or non-human animals from said genetically modified or abnormal reprogrammed cells or from genetically modified or abnormal cells reprogrammed by serial nuclear addition with or without nuclear transfer.

Cells, cell lines, tissues and organs may be produced from the reprogrammed cells by any suitable technique.

Cells, cell lines, tissues and organs may also be generated from an animal embryo that has developed from said reprogrammed cells. Cells, cell lines, tissues, organs, animal embryos or cell lines derived from such an embryo may also be generated from cells reprogrammed by serial nuclear addition with or without nuclear transfer.

In a particularly preferred embodiment of the present invention normal, abnormal, diseased or genetically modified cells may be reprogrammed and cells cell lines, tissues, organs, embryos, non-human foetuses or animals established from these reprogrammed cells. In addition cells, cell lines, tissues and organs may be generated from an animal embryo, non-human foetus or animal that has developed from a reprogrammed cell. These cells and cell lines may be used for cell based gene and tissue therapies, cell based gene and drug screening, diagnostics, basic and applied research, and the production of non-human animals.

Reprogrammed cells or cells derived from reprogrammed cells may be transferred to an animal to restore function to, or improve the function of tissues or organs that have been damaged, for example by disease, injury or aging, or are dysfunctional due to genetic disease.

In a particularly preferred embodiment, cells or cell lines may be established from a patient's own cells. Cells or cell lines may also be established from an embryo or embryonic cell generated by reprogramming a patients own cell. This approach is known as therapeutic cloning and offers the opportunity to treat a wide range of medical conditions including, but not limited to, spinal cord injury, diabetes and Alzheimers disease. Cells or cell lines established by therapeutic cloning would be genetically identical to the patient and would pose little or no risk of immune rejection following transplantation.

Applicant has discovered that by incubating a partially or completely differentiated donor cell or nucleus in the environment of a suitable recipient cell the donor cell or nucleus may be reprogrammed. For example it may be de-differentiated to produce, for example, a pluripotent cell such as an embryonic stem cell. More particularly, Applicant has discovered that it is possible to generate ES cells by nuclear addition-mediated reprogramming of adult somatic cell nuclei and that ES cells derived by NA-mediated reprogramming of cumulus cells (CC-ES cells) retain the capacity to differentiate into multiple cell types both in vitro and in vivo (see FIGS. 1, 2, and 3).

Whilst Applicant does not wish to be restricted by theory, it is postulated that the recipient cell may provide factors which cause the donor cell to be reprogrammed, for example to at least partially de-differentiate to form pluripotent cell lines.

Accordingly, in a further aspect of the present invention, there is provided a method of restoring or improving function of a tissue or organ, said method including providing
an animal, and
one or more reprogrammed cells according to the present invention or derivatives of said reprogrammed cells;
transferring the cells or derivatives of the reprogramed cells to the animal, preferably at or near the site of said tissue or organ; and
allowing the transferred cells or derivatives of the reprogrammed cells to repopulate said tissue or organ.

There is also provided use of a reprogrammed cell according to the present invention or derivative thereof for preparation of a medicament for restoring or improving function of a tissue or organ by cell based therapies.

The cells or cell lines which have been genetically modified may be transferred to an animal to deliver gene therapy. Gene therapy would enable treatment of diseases such as but not limited to Sickle cell anaemia, haemophilia, metabolic disorders, liver disease, AIDS and other infectious diseases as well as assisting in the repair or reconstitution of tissues or organs that have been damaged, for example by disease, injury or aging.

In a still further aspect of the present invention, there is provided a method of gene therapy, said method including
  providing
    an animal, and
    one or more genetically modified, reprogrammed cells according to the present invention or derivatives of said cells;
  transferring the cells or derivatives of the reprogramed cells to the animal; and
  allowing said cells or derivatives of the reprogramed cells to repopulate in said animal to provide gene therapy.

There is also provided use of a genetically modified or abnormal reprogrammed cell according to the present invention or derivative thereof for preparation of a medicament for gene therapy.

The cells of the present invention may also be used for investigating disease processes and in gene and drug screening assays for characterised or uncharacterised multigenic diseases. In this case, the cells or cell lines are preferably derived on a patient or disease specific basis. The cells or cell lines may be established following reprogramming of a cell from an animal, or a cell culture or cell line established from an animal suffering a genetic disease. Abnormal cells include cells with known or unknown gene or chromosomal mutations, deletions, rearrangements and/or duplications. The reprogrammed cells and cells, tissues and organs derived from the reprogrammed cells, may be used to investigate a disease process, assess the therapeutic value, efficacy or toxicity of a particular drug, gene or treatment regime, and subsequent to genetic correction or modification, to deliver gene and tissue therapies.

Accordingly, in a further aspect of the present invention, there is provided a method of investigating disease mechanisms, processes and potential or existing therapies by establishing cell-based screening assays to identify and evaluate candidate drug targets and therapeutic genes and to identify and evaluate drugs and drug candidates, said method including
  providing
    one or more reprogrammed cells according to the present invention or derivatives of said cells;
    monitoring, adding, removing or otherwise investigating or modifying cellular processes including but not limited to gene expression and gene products expressed in the cells for the investigation; and/or
    adding, removing or otherwise investigating the biological effect of chemicals and potential drugs on cellular processes of the reprogrammed cell or derivatives thereof.

There is also provided use of a reprogrammed cell according to the present invention or derivative thereof for evaluating the usefulness of a medicament to treat multigenic diseases.

There is also provided use of a reprogrammed cell according to the present invention or derivative thereof for preparation cells, cell lines or their derivatives for medical and/or basic research.

Accordingly, in a further aspect of the present invention, there is provided a method of establishing cells or cell lines for medical and/or basic research, said method including
  providing
    one or more reprogrammed cells according to the present invention or derivatives of said cells;
    monitoring, adding, removing or otherwise investigating or modifying cellular processes including but not limited to gene expression and gene products expressed by the cells or derivatives thereof for the investigation of gene products and chemicals as potential therapeutic targets or agents.

There is also provided use of a reprogrammed cell according to the present invention or derivative thereof for medical and/or basic research.

The methods of the present invention may include the still further step of generating non-human animals from said reprogrammed animal cells or embryos or non-human transgenic animals from said transgenic animal cells or embryos.

Animal embryos may be generated from the reprogrammed cells by any suitable method. Embryonic development may be initially in vitro and subsequently in a surrogate. Thus, the aneuploid cell may be initially cultured in vitro to produce an embryo consisting of a diploid cell or a mixture of diploid and aneuploid cells as and then the embryo may be transferred to a surrogate for subsequent development into a non-human animal. In vitro culture of the cells may be in any suitable medium.

The animal embryo may be of any type, and includes bird, fish, reptile and mammalian (including ungulate and primate), for example murine, bovine, ovine or porcine embryos. The non-human animal may also be of any type, and includes bird, fish, reptile and mammalian (including ungulate and primate), for example murine, bovine, ovine or porcine animals. Preferably, the animal embryo or animal is a porcine embryo or animal, bovine embryo or animal, a ovine embryo or animal or a murine embryo or animal.

In a further aspect of the present invention there is provided a reprogrammed cell or cell line, genetically modified reprogrammed cell or cell line, or genetically abnormal reprogrammed cell or cell line produced by the methods of the present invention. The cell or cell line may be a human or non-human cell or cell line. Preferably the cell or cell line is a porcine, murine, ovine, bovine, caprine or human cell or cell line.

Examples of cells and cell lines which may be produced by the methods of the present invention include pluripotent cells such as embryonic and somatic stem cells and precursor cells or their derivatives including any end stage differentiated cell.

In a further aspect of the present invention there is provided an isolated tissue or organ produced or improved by the methods of the present invention. The tissue or organ may be of any animal species. Preferably the tissue or organ is a porcine, murine, ovine, bovine, caprine, primate or human tissue or organ.

In a further aspect of the present invention there is provided an animal embryo or transgenic animal embryo produced or improved by the methods of the present invention. The animal embryo or transgenic animal embryo may be human or non-human. Preferably the animal embryo or transgenic animal embryo is a porcine, murine, ovine, bovine, caprine, primate or human embryo.

In a still further aspect of the present invention there is provided a non-human animal or transgenic non-human animal produced or improved by the methods of the present invention. Preferably the non-human animal or non-human transgenic animal is a porcine, murine, ovine, bovine or caprine animal. These non-human animals may provide organs for transplantation into humans or other forms of xenotransplantation.

In a still further aspect of the present invention there is provided an animal product from a non-human animal or a non-human transgenic animal produced by the methods of the present invention. The animal product may be a human or other animal protein or gene product, or a mixture of human and non-human animal products.

In a further aspect of the present invention there is provided a method of generating an animal embryo which method includes
   providing
      a donor nucleus, and
      a recipient cell;
   introducing the donor nucleus into the recipient cell to produce an aneuploid cell;
   optionally subjecting the aneuploid cell to an activation step;
   generating a reprogrammed diploid cell from said aneuploid cell by removal, destruction or loss of the recipient cell nucleus or nuclear DNA from said aneuploid cell; and
   generating an animal embryo from the said reprogrammed diploid cell.

Accordingly, the method of the present invention involves nuclear addition, ie. the addition of the nucleus of one cell to another cell.

Whilst Applicant does not wish to be restricted by theory, it is postulated that disproportionate distribution of the recipient cell's metaphase plate, nucleus, pronucleus, chromatin, chromosomes or DNA in the daughter cells of the aneuploid cell, or expulsion of the recipient cell's metaphase plate, nucleus, pronucleus, chromatin, chromosomes or DNA from the aneuploid cell or one or more of the aneuploid cell's daughter cells, results in the formation of a diploid animal embryo and placenta or a diploid animal embryo and an aneuploid placenta. An aneuploid placenta may provide advantages over normal diploid placentas. For example, the aneuploid placenta may be bigger and more vigorous, which may in turn improve embryo viability. Alternatively the nucleus of the recipient cell may be expelled from the cell and participate no further in the development of the embryo.

The process of the present invention may include the further step of generating a non-human animal from the animal embryo.

In a still further aspect of the present invention there is provided a method of generating a transgenic animal embryo said method including
   providing
      a donor nucleus which has been genetically modified to eliminate or reduce an undesirable activity or to provide for, or increase, a desirable activity, and
      a recipient cell;
   adding the donor nucleus to the recipient cell to produce a genetically modified aneuploid cell;
   optionally subjecting the aneuploid cell to an activation step;
   generating a reprogrammed diploid cell from said aneuploid cell by removal, destruction or loss of the recipient cell nucleus or nuclear DNA from said aneuploid cell; and
   generating a transgenic animal embryo from the said reprogrammed diploid cell.

In a preferred aspect of the present invention, the method may include
   subjecting the metaphase plate, nucleus, pronucleus, chromatin, chromosomes or DNA of the recipient cell to a pre-treatment step, as hereinbefore described.

In one form of this aspect of the present invention, the method may include the further step of
substantially removing or substantially destroying the nucleus, pronucleus, metaphase plate, chromatin, chromosomes or DNA of the recipient cell, preferably prior to division of the aneuploid cell, as hereinbefore described.

In an alternate form, the method includes the further steps of
   providing a co-mingling inhibitor, and
   subjecting the aneuploid cell to a co-mingling inhibitor for a period sufficient to reduce or eliminate co-mingling of the recipient cell DNA and introduced DNA, as hereinbefore described.

Loss or removal of the recipient cell's metaphase plate, nucleus, chromatin, chromosomes or DNA may be assessed, as hereinbefore described.

In an alternate form of this aspect of the invention the recipient cell may be enucleated simultaneously with introduction of the donor cell or nucleus, as hereinbefore described.

The methods of the present invention may include the further step of subjecting the recipient cell, aneuploid cell or diploid cell to an activation step, as hereinbefore described.

The aneuploid cell is preferably maintained in a suitable environment for a time sufficient to allow the donor nucleus or cell to be reprogrammed, as hereinbefore described.

The donor nucleus and recipient cell which are used in the method of the present invention may be of any suitable origin, as hereinbefore described.

In preferred embodiments, the methods of the present invention may include producing reprogrammed second cells, and use of serial nuclear addition or a combination of nuclear addition and nuclear transfer, as hereinbefore described.

In a preferred embodiment, the methods of the present invention may include the further step of
   maintaining the aneuploid cell in a suitable medium for a period sufficient to allow the cell to recover a substantially normal shape, prior to activation.

Applicant has discovered that the number of viable embryos produced may be significantly increased by permitting the aneuploid cell to be maintained in culture for a period sufficient to allow the cell to recover a substantially normal, e.g. generally circular, shape. This culture step may be undertaken in a manner similar to that described herein.

Whilst applicant does not wish to be restricted by theory, it is postulated that the culture period permits the aneuploid cell to return to a more normal or stable state.

The aneuploid cell may be maintained in a suitable medium preferably for a period of approximately 3 to 8 hours, more preferably approximately 4.5 to 6 hours. It is desirable, however, that the culture period end before any, or any substantive division, ensues.

In a still further aspect of the present invention there is provided a method of preparing an aneuploid or reprogrammed diploid cell which method includes
   providing
      a donor nucleus;
      an exogenous nucleic acid molecule, and
      a recipient cell;
   introducing the donor nucleus and the exogenous nucleic acid molecule into the recipient cell to produce an aneuploid; and
   optionally generating a reprogrammed dipliod cell from said aneuploid cell by removal, destruction or loss of the recipient cell nucleus or nuclear DNA.

In a further aspect of the present invention there is provided a method of generating a transgenic animal embryo which method includes providing
a donor nucleus,
an exogenous nucleic acid molecule, and
a recipient cell;
introducing the donor nucleus and the exogenous nucleic acid molecule into the recipient cell to produce an anueploid cell; and
optionally generating a reprogrammed diploid cell from said aneuploid cell by removal, destruction or loss of the recipient cell nucleus or nuclear DNA; and;
generating a transgenic animal embryo from the diploid cell.

The step of introducing the donor nucleus and the exogenous nucleic acid molecule into the enucleated or non-enucleated recipient cell is preferably performed by either:
1) introducing the exogenous nucleic acid molecule into the donor nucleus and then introducing the donor nucleus into the recipient cell;
2) combining the exogenous nucleic acid molecule with the donor nucleus and introducing the combined nucleic acid and nucleus into the recipient cell; or
3) introducing the exogenous nucleic acid and the donor nucleus separately into the recipient cell.

The exogenous nucleic acid molecule may be introduced into the donor nucleus or recipient cell by any suitable means. For example, direct injection, electroporation or simple bathing of the nucleus or cell in a solution of the exogenous nucleic acid may be used.

In particularly preferred embodiments the exogenous nucleic acid is directly injected into the donor nucleus prior to nuclear addition; or alternatively the donor nucleus and exogenous nucleic acid are combined and then injected into the recipient cell.

The exogenous nucleic acid molecule may be of any suitable type. Preferably it is a naked DNA molecule. Additionally exogenous RNA, mRNA, hybrids of DNA and RNA and ribozymes maybe used. Whilst applicant does not wish to be restricted by theory, it is thought that when such molecules are introduced into or taken up by the donor nucleus, transgenesis may occur by random integration or by homologous recombination.

Alternatively, targeted transgenesis may be used, in which case the exogenous nucleic acid molecule includes 5' and/or 3' ends which direct the nucleic acid molecule to specific site(s) within the donor nucleus genome.

The method of the present invention may include the further step of generating a non-human transgenic animal from the transgenic animal embryo.

The donor nucleus may be of any suitable type and from any suitable species, as hereinbefore described.

The recipient cell may be of any suitable type and from any suitable species, as hereinbefore described.

The donor nucleus may be transferred to the recipient cell by any suitable method, as hereinbefore described.

Recipient cell volume may be increased by fusing together a zona pellucida free recipient cell with an enuecleated oocyte or other cytoplast before, after or at approximately the same time as donor nucleus fusion.

An animal embryo may be generated from the reconstituted cell by any suitable method, as hereinbefore described.

The animal embryo or non-human animal may be of any type, as hereinbefore described.

The donor nucleus and recipient cell which are used in the method of the present invention may be of any suitable origin, as hereinbefore described.

The method of the present invention may be used to generate transgenic non-human animals, as hereinbefore described.

In a further aspect of the present invention there is provided a reconstituted animal cell produced by the methods of the present invention. The cell may be human or non-human. Preferably the reconstituted animal cell is a porcine, murine, ovine, bovine, caprine or human cell.

In a further aspect of the present invention there is provided a transgenic animal embryo produced by the methods of the present invention. The embryo may be human or non-human. Preferably the transgenic animal embryo is a porcine, murine, ovine, bovine, caprine or human embryo.

In a still further aspect of the present invention there is provided a non-human transgenic animal produced by the methods of the present invention. Preferably the transgenic animal is a porcine, murine, ovine, bovine or caprine animal.

The present invention will now be more fully described with reference to the accompanying Examples and Drawings. It should be understood, however, that the description following is illustrative only and should not be taken in any way as a restriction on the generality of the invention described above.

In the Figures:

FIG. 1: Parental CC-ES cells displayed characteristic mouse ES cells colony morphology (a), SSEA-1 expression (b) and alkaline phosphatase activity (c). Distinctive X-gal stained nuclei (d) and female (40,XX) karyotype (e) confirmed contribution of the transgenic donor cell nucleus. Absence of Y chromosome-specific PCR product (lower band) in parental CC-ES cells and four clonally-derived CC-ES cell sub-lines (f). Controls: male ZIN40 ES cells, male foetal fibroblast (mFF) cells and no DNA (water). Scale bar, 100 μm.

Figure 2:
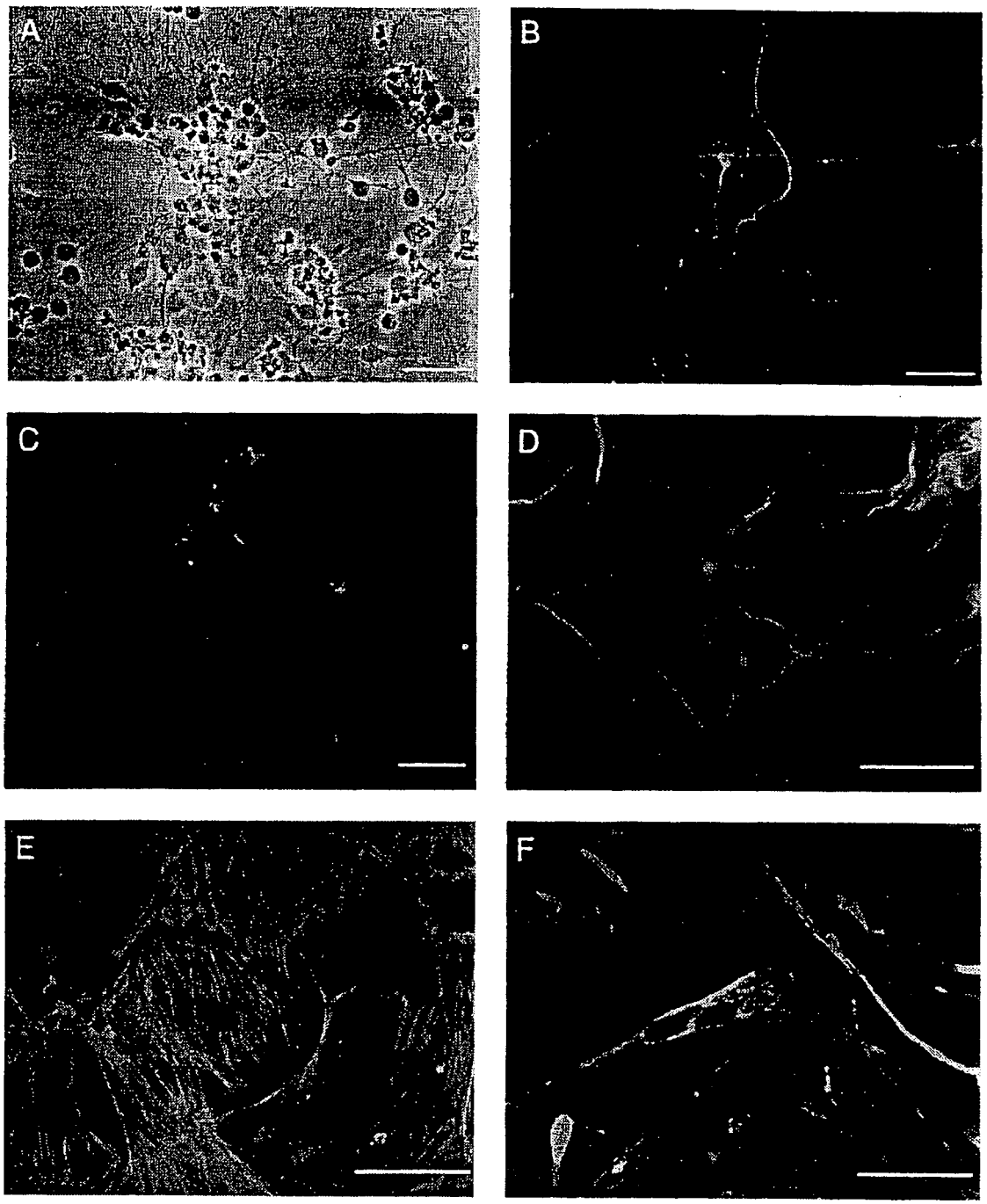

FIG. 2: Neural (a-d) and myogenic (e-f) cells derived by in vitro differentiation of clonally derived CC-ES cells. Morphology was confirmed by indirect immunofluorescence to neurone-specific proteins: neurofilament 160 and 68 kDa (b and c) and MAP-2 (d), and muscle-specific proteins: actin (e) and desmin (f). Scale bar, 50 μm.

Figure 3:
Figure 3:
Figure 3:
Figure 3:
Figure 3:
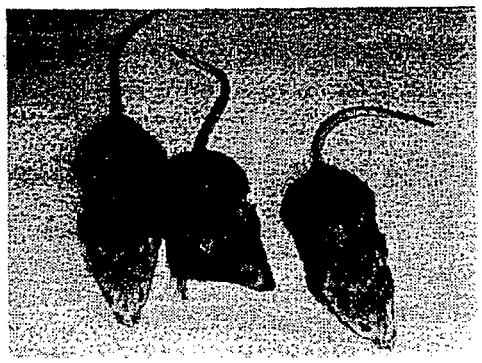
Figure 3:
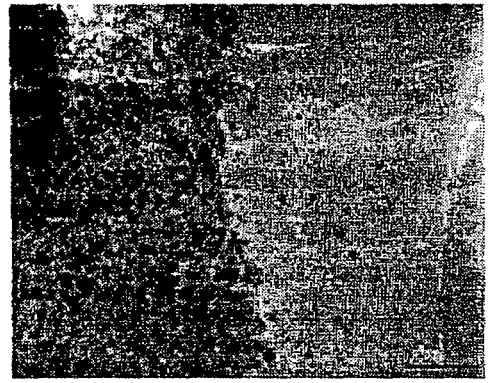
Figure 3:
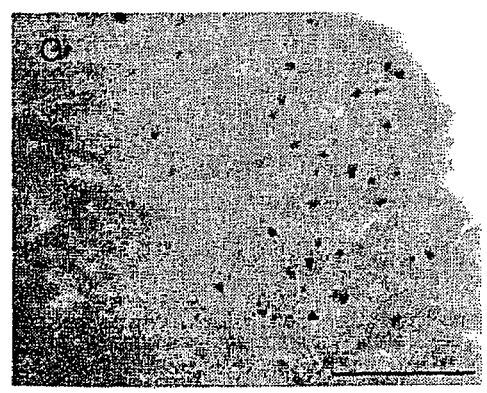
Figure 3:
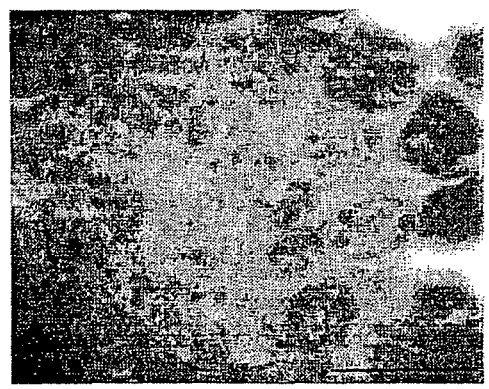

FIG. 3: CC-ES cell differentiation in vivo. Histological examination (H&E) of parental CC-ES teratocarcinomas show the presence of ectoderm: neural epithelium (a) and stratified squamous epithelium (b); mesoderm: muscle and bone (c); and endoderm: ciliated epithelium (d). Extensive somatic cell contribution of parental CC-ES cells in chimaeric pups (left and right) was indicated by coat colour (e) and confirmed by distinctive X-gal stained nuclei in brain (f), heart (g) and gut (h) (PAS counterstained). Scale bar, 100 μm.

EXAMPLE 1

Comparison of Sequence of Enucleation and Direction Injection in Mouse Nuclear Transfer Conventional Order: Enucleation Followed by Injection
In five replicate experiments:
of manipulated oocytes survived enucleation (84/138)
of these survived piezo-assisted direct injection with cumulus cell nuclei (16/78)
resulting in only 12% manipulated oocytes placed into culture (16/138)

Reversed Order: Injection then Enucleation
In five replicate experiments:
of manipulated oocytes survived piezo-assisted direct injection with cumulus cell nuclei (129/236)

of these survived enucleation (86/118)
resulting in 36% manipulated oocytes placed into culture (86/236)

All experiments were performed with oocytes and cumulus cells from standard F1 (C57BU6xCBA) mice.

EXAMPLE 2

Isolation of Pluripotent Embryonic Stem Cells from Reprogrammed Adult Somatic Cell Nuclei: A Murine Model for Human Therapeutic Cloning Pluripotent human stem cells isolated from early embryos represent a potentially unlimited source of many different cell types for cell-based gene and tissue therapies (1-3). However, the significant problem of donor-recipient tissue matching will need to be addressed if the full potential of donor embryo-derived cell lines is to be realised. One approach which avoids issues of transplant rejection would be to establish stem cell lines from the patient's own cells through therapeutic cloning (3,4). Recent studies have shown that it is possible to take the nucleus from an adult somatic cell, transfer the nucleus to an unfertilised oocyte devoid of maternal chromosomes, and achieve embryonic development directed by the transferred nucleus (5,6). Stem cells isolated from such a cloned embryo would be genetically identical to the patient and pose no risk of immune rejection. Here we report the isolation of pluripotent murine stem cells from reprogrammed adult somatic cell nuclei. Nuclear addition embryos were generated by direct injection of mechanically isolated cumulus cell nuclei into mature oocytes. Embryonic stem (ES) cells isolated from nuclear addition blastocysts displayed characteristic morphology and marker expression and underwent extensive differentiation into all three embryonic germ layers (endoderm, mesoderm and ectoderm) in tumours and in chimaeric foetuses and pups. Nuclear addition ES cells also readily differentiated into neurones and muscle in culture. This study shows that pluripotent stem cells can be derived from terminally differentiated adult somatic cell nuclei and offers a model system for the investigation of nuclear donor potential in the development of autologous, human pluripotent stem cell therapies.

Results and Discussion

Blastocysts were generated by substituting cumulus cell nuclei for the genetic material of mature oocytes using a modification of the method previously described (6). The cumulus cells were collected from transgenic mice (ZIN40) that ubiquitously express a nuclear localised lacZ reporter gene and demonstrate distinctive blue staining when treated with X-gal substrate (7). As recipient oocytes were collected from a non-transgenic strain (B6D2F1), the presence of the lacZ transgenic marker was used to demonstrate nuclear contribution of the cumulus cell nuclei following transfer (8). Thirty-nine percent (362/926) of manipulated oocytes survived injection and enucleation in 21 replicate experiments. Following strontium activation, 75% (270/362) of the reconstructed oocytes cleaved to the two-cell stage after 24 hours culture. Ten (3%) morphologically normal cumulus cell (CC)-derived blastocysts formed after 96 hours culture and were placed into culture for ES cell isolation. Eight blastocysts hatched and formed obvious inner cell mass outgrowths with 3 displaying putative ES cell morphology in initial passages. One cell line was established (parental CC-derived ES cell line) and continued to display characteristic mouse ES cell morphology when grown in the presence or absence of a fibroblast feeder layer in leukemia inhibitory factor (LIF) supplemented media (FIG. 1a). Four sub-lines were established from 48 individual, mechanically isolated cells from the parental CC-derived ES (CC-ES) cell line.

All CC-ES cell lines examined showed characteristic ES cell morphology (FIG. 1a) and expressed characteristic mouse ES cell markers including stage-specific embryonic antigen-1 (SSEA-1) (FIG. 1b) and alkaline phosphatase activity (FIG. 1c). Oct4 mRNA was highly expressed in undifferentiated ES cells and down regulated in differentiated ES cell cultures (not shown). NT-ES cells were demonstrated to have been derived from a reprogrammed somatic nucleus by distinctive blue X-gal stained nuclei (FIG. 1d) and a normal female (40,XX) karyotype (FIG. 1e). In addition to the cytological examination, the parental CC-ES cells and clonally derived sub-lines were shown to lack a Y chromosome-specific genomic PCR product (FIG. 1f). No other female ES cells have been grown in our laboratory. The rate of ES cell derivation from CC blastocysts was similar to preliminary experiments where 5 ES cell lines were established from 55 in vivo derived blastocysts (3.5 days post coitum (dpc)).

Pluripotency of the parental CC-ES cell line and two of the clonally derived sub-lines was investigated in vitro and in vivo. All CC-ES cell lines were found to readily differentiate into neurones and beating muscle in vitro at a similar frequency to control ES cells. Morphological observations were confirmed by indirect immuno-fluorescence in differentiated CC-ES cell cultures using neuronal- and muscle-specific antibodies (FIG. 2). There appeared to be no restriction in differentiation with all CC-ES cell injection sites (12/12) in immunocompromised mice yielding lacZ positive teratocarcinomas with extensive differentiation into all three embryonic germ layers including neural epithelium and stratified squamous epithelium (ectoderm); muscle, cartilage and bone (mesoderm); and ciliated secretory epithelium (endoderm) (FIGS. 3a-d).

Restoration of pluripotency to the somatic nucleus was further demonstrated by somatic cell contribution in chimaeric foetuses and pups. Four out of six midgestation (1 0dpc) foetuses contained X-gal positive cells. One foetus appeared to be composed solely of NT-ES cell derivatives (not shown). Six out of 14 pups were identified as chimaeric by obvious coat and eye colour (FIG. 3e). Multi-lineage CC-ES cell contribution was confirmed by lacZ genomic PCR (not shown) and microscopic analysis of X-gal stained frozen sections of all organs analysed including cerebellum, heart and gut (FIGS. 3f-h).

This report describes the first isolation of pluripotent stem cells from adult somatic cell nuclei. While ES-like cells have been isolated from bovine nuclear transfer embryos derived from foetal fibroblast nuclei (9), the mouse somatic cell-derived ES cell research described in this report offers a more accessible and diversified model system for in vitro and in vivo investigation of nuclear reprogramming and developmental competence. For example, ES cell lines may be established from different donor cell types and evaluated for possible restrictions in pluripotency using established in vitro and in vivo ES cell differentiation regimes. Such analyses may help explain the limited development of nuclear transfer blastocysts derived from neuronal and Sertoli cell nuclei (6). These studies could also be enhanced through the use of established transgenic mouse lines which harbour developmentally regulated or ubiquitously expressed reporter genes to monitor reprogramming at the molecular level or visualise cellular contribution in chimaeric embryos (8). Similarly, mutant mouse lines with specific gene deletions or genetic modifications could be used as a nuclear donor source to investigate the role of specific genes in nuclear reprogramming or pluripotent stem cell differentiation.

Possibly the greatest potential for combining nuclear reprogramming with ES cell derivation lies in the development of autologous human pluripotent stem cells for cell based gene and tissue therapies. ES cell derived somatic cell transplantation could restore function to diseased or damaged tissues or be genetically altered prior to transplantation to deliver gene therapy. Transplantation studies in the mouse have shown that ES cell-derived cardiomyocytes (10), neural precursors (11), haematopoietic precursors (12) and insulin-secreting cells (13) can survive and function in recipient animals. Research described in this report provides proof of principal for human therapeutic cloning in a model system.

Supplementary Material and Methods

Generation of Blastocysts by Direct Nuclei Injection

Oocytes and cumulus cells were collected from superovulated adult C6D2F1 (C57BU6J×DBA/2) and ZIN40/129Sv female mice, respectively. Individual cumulus cell nuclei were mechanically isolated and injected into intact metaphase II oocytes (13 to 15 h after human chorionic gonadotrophin administration) using piezo-assisted micromanipulation (Piezo impact micromanipulation system, PMM-150FU; Prime Tech Ltd., Ibaraki, Japan). Cytoplasm containing the metaphase plate of each injected oocyte was then removed in the presence of cytochalasin B (Sigma, St. Louis, Mo.), stained with bisBENZIMIDE (Hoechst 33342; Sigma) dye and assessed under ultraviolet light for removal of only the oocyteis chromosomes. After 3 to 4 h reconstructed oocytes were chemically activated in 10 mM strontium chloride (Sigma) in the presence of cytochalasin B for 5 h, then cultured in G1/G2 medium (14) at 37° C. and 5% $CO_2$ for 4 days with embryo development assessed daily.

Derivation of ES Cells

ES cells were isolated essentially as described (15) with the exception that all embryos were cultured in individual wells of 96-well tissue culture plates (Falcon, Becton Dickinson Labware, Lincoln Park, N.J.). The zona pellucida on some blastocysts were slit with a fine glass pipette to assist in hatching. ES cell isolation was performed in high glucose Dulbecco's modified Eagle's medium (Trace Bioscientific, Castle Hill, Australia) containing 20% foetal bovine serum (CSL, Melbourne, Australia) and $2 \times 10^3$ U/ml LIF (gift from Lindsay Williams, Monash University, Clayton, Australia) with non-essential amino acids, glutamine, penicillin/streptomycin (Life Technologies, Gaitherburg, Md.) and 2-mercaptoethanol (Sigma) at standard concentrations (16). Once established, ES cells were cultured without feeder cells in gelatin-coated dishes in ES cell culture medium containing 10% foetal bovine serum. Clonal sub-lines were established by mechanically transferring individual cells from passage 6, feeder-free, parental CC-ES cell cultures into separate gelatin-coated wells of a 96-well plate.

Characterisation of ES Cells

Alkaline phosphatase activity was demonstrated as previously described (17).

SSEA-1 expression was detected by SSEA-1 specific monoclonal antibody (MC-480; Developmental Studies Hybridoma Bank, Iowa City, Iowa) and visualised by fluorescein isothiocyanate conjugated goat anti-mouse immunoglobulin (Dako, Carpinteria, Calif.).

Oct4 RT-PCR was performed as previously described (18) using modified primers: SEQ ID NO:15'-GTTCTCTTTG-GAAAGGTGTTC-3' (forward) and SEQ ID NO:2 5'-ACTC-GAACCACATCCTTCTC-3' (reverse) where the anticipated Oct4 RT/PCR product size was 311 bp. As a control for mRNA quality we assayed polyA transcripts using the same RT-PCR conditions and the following primers: SEQ ID NO:3 5'-GTTGCAGGGTAACCGATGAA-3' (forward) and SEQ ID NO:45'-TGTTGTGGGTATGCTGGTGT-3' (reverse) and the anticipated product size was 361 bp.

Standard G-banding techniques were used for karyotyping (50 metaphase spreads counted). The lack of a Y chromosome was further confirmed by the absence of Smcy (19) as determined by genomic PCR using primers: SEQ ID NO:5 5'-TGAAGCTTTGGCTTTGAG-3' (forward) and SEQ ID NO:6 5'-CCGCTGCCAAATTCTTTGG-3' (reverse) under the following conditions: 35 cycles of 95° C. for 30 seconds, 58° C. for 30 seconds, 72° C. for 30 seconds (Dr David Threadgill, Department of Cell Biology, Vanderbilt University, Nashville, Tenn.; personal communications). PCR products were generated from Smcy (approximately 290 bp) and its X-chromosomal homologue Smcx (approximately 330 bp).

Teratocarcinoma Formation

Teratocarcinomas were established by injection single cell suspension of CC-ES (parental and clonal) cells under the testis capsule of 4- to 6-week-old severe combined immunodeficient (SCID) mice. Testes were removed 18 to 20 days after surgery and portions either snap-frozen for X-gal staining or fixed in Bouinfs fixative, embedded in paraffin and examined histologically after haematoxylin and eosin staining.

Generation of Chimaeric Foetuses and Pups

Chimaeras were generated by morula aggregation (20) or blastocyst injection (21). Parental CC-ES cells were either aggregated with eight-cell CD1 embryos or injected into C57BL/6J blastocysts (3.5dpc) before transfer to pseudopregnant recipient B6CBF1 (C57BI/6J×CBA) mice (2.5dpc).

In Vitro Differentiation and Characterisation

CC-ES cell aggregates were either treated with retinoic acid for neuronal differentiation (22) or allowed to spontaneously differentiate into beating muscle (23). Characteristic antigens in differentiated ES cells were detected by indirect immunofluorescence using the specific monoclonal primary mouse antibodies and FITC conjugated anti-mouse immunoglobulin (Dako) at the following dilutions according to manufacturer's instructions: anti-actin (1:20; M0635, Dako), anti-desmin (1:30; M0760, Dako), anti-MAP 2a,b (1:100; AP20, Neomarkers, Union City, Calif.) and anti-neurofilament proteins 68 kDa and 160 kDa (neat; Amersham Pharmacia Biotech, Amersham, UK and Boehringer Mannheim Biochemica, Indianapolis, Ind., respectively).

X-gal Staining/lacZ PCR

Embryos and frozen tissue sections were fixed and stained with 5-bromo-4-chloro-3-indoly β-D-galactopyranoside (X-gal; Promega, Madison, Wis.) substrate as previously described (24). The presence of lacZ was detected by genomic PCR using the following primers: SEQ ID NO:7 5'-ACTATCCCGACCGCCTTACT-3' (forward) and SEQ ID NO:8 5'-TAGCGGCTGATGTTGAACTG-3' (reverse) under the following conditions: 30 cycles of 95° C. for 30 seconds, 52° C. for 30 seconds, 72° C. for 2 minutes. The anticipated product size was 172 bp.

EXAMPLE 3

Efficiency of Nuclear Transfer and Nuclear Addition in Pigs

TABLE 1

| Group | Oocytes | Fused (%) | Cleaved (%) | Blastocysts (%) |
|---|---|---|---|---|
| NT | 97 | 44(45.4) | 21(47.7) | 6(13.6) |
| NA | 112 | 54(48.2) | 44(81.5) | 17(31.5) |

Following NT and NA a period of 6 hours was allowed prior to undertaking Activation/Fusion.
NT: Nuclear transfer
NA: Nuclear addition.

EXAMPLE 4

Efficiency of Nuclear Addition in Pigs and Effect of Activation, Fusion and Post Treatment Thereon The nuclear addition of Example 3 was repeated except that a series of modifications were introduced to gauge their impact on efficiency. These included utilising intact MI oocytes in place of MII oocytes, varying the order and arrangement of the activation and fusion steps, utilising chemical inhibitors to prevent co-mingling, and removing or destroying genomic DNA. The results are provided in Table 2.

TABLE 2

Nuclear addition

| Qocyte Source | Nuclear manipulation | | Post Treatment[1] | Ploidy Correction Intervention | Reconstructed Embryos | Development to Blastocyst (%) |
|---|---|---|---|---|---|---|
| Intact MII oocytes (non enucleated) | Simultaneous Fusion[2] and Activation[3] | | Development is allowed to continue without further intervention | | 360 | 116 (32) |
| | | | | [5]Remove or Destroy genomic DNA | 120 | 28 (23) |
| | | | 1. Cytokinesis Inhibitors (eg Cytochalasin B) | | 60 | 15 (25) |
| | | | 1. Cytokinesis Inhibitors (eg Cytochalasin B) | [5]Remove or Destroy genomic DNA | 65 | 14 (21) |
| | | | 2. Karyokinesis Inhibitors (eg Colcemid, Nocodazole or Taxol) | | 57 | 14 (25) |
| | | | 2. Karyokinesis Inhibitors (eg Colcemid, Nocodazole or Taxol) | [5]Remove or Destroy genomic DNA | 43 | 6 (14) |
| | | | Combination 1 + 2 | | 48 | 7 (15) |
| | | | Combination 1 + 2 | [5]Remove or Destroy genomic DNA | 36 | 4 (12) |
| Intact MII oocytes | Activation[3] | Fusion[2] | Development is allowed to continue without further intervention | | 126 | 30 (24) |
| | | | | [5]Remove or Destroy genomic DNA | 48 | 8 (17) |
| Intact MII oocytes | Cell Insertion/ Injection (w/out fusion[4]) | Activation[3] | Development is allowed to continue without further intervention | | 53 | 16 (30) |
| | | | | [5]Remove or Destroy genomic DNA | 48 | 12 (25) |
| | | | 1. Cytokinesis Inhibitors (eg Cytochalasin B) | | 36 | 3 (8) |
| | | | 1. Cytokinesis Inhibitors (eg Cytochalasin B) | [5]Remove or Destroy genomic DNA | 29 | 3 (10) |
| | | | 2. Karyokinesis Inhibitors (eg Colcemid, Nocodazole or Taxol) | | 31 | 5 (16) |
| | | | 2. Karyokinesis Inhibitors (eg Colcemid, Nocodazole or Taxol) | [5]Remove or Destroy genomic DNA | 26 | 4 (15) |
| | | | Combination 1 + 2 | | 24 | 3 (12) |
| | | | Combination 1 + 2 | [5]Remove or Destroy genomic DNA | 18 | 2 (11) |
| Intact MI oocytes (non enucleated) | Simultaneous Fusion[2] and Activation[3] | | Development is allowed to continue without further intervention | | 65 | 3 (5) |
| | | | | [5]Remove or Destroy genomic DNA | 46 | 2 (4) |
| | | | 1. Cytokinesis Inhibitors (eg Cytochalasin B) | | 38 | 1 (3) |
| | | | 1. Cytokinesis Inhibitors (eg Cytochalasin B) | [5]Remove or Destroy genomic DNA | 27 | 2 (7) |
| | | | 2. Karyokinesis Inhibitors (eg Colcemid, Nocodazole or Taxol) | | 26 | 3 (11) |
| | | | 2. Karyokinesis Inhibitors (eg Colcemid, Nocodazole or Taxol) | [5]Remove or Destroy genomic DNA | 18 | 1 (6) |
| | | | Combination 1 + 2 | | 23 | 1 (4) |
| | | | Combination 1 + 2 | [5]Remove or Destroy genomic DNA | 17 | 1 (6) |

TABLE 2-continued

Nuclear addition

| Qocyte Source | Nuclear manipulation | | Post Treatment[1] | Ploidy Correction Intervention | Reconstructed Embryos | Development to Blastocyst (%) |
|---|---|---|---|---|---|---|
| Intact MI oocytes | Activation[3] | Fusion[2] | Development is allowed to continue without further intervention | | 42 | 3 (7) |
| | | | | [5]Remove or Destroy genomic DNA | 28 | 2 (7) |
| Intact MI oocytes | Cell Insertion/ Injection (w/out fusion[4]) | Activation[3] | Development is allowed to continue without further intervention | | 43 | 3 (7) |
| | | | | [5]Rmover or Destroy genomic DNA | 36 | 2 (5) |
| | | | 1. Cytokinesis Inhibitors (eg Cytochalasin B) | | 27 | 1 (4) |
| | | | 1. Cytokinesis Inhibitors (eg Cytochalasin B) | [5]Remove or Destroy genomic DNA | 25 | 1 (4) |
| | | | 2. Karyokinesis Inhibitors (eg Colcemid, Nocodazole or Taxol) | | 19 | 1 (5) |
| | | | 2. Karyokinesis Inhibitors (eg Colcemid, Nocodazole or Taxol) | [5]Remove or Destroy genomic DNA | 15 | 1 (7) |
| | | | Combination 1 + 2 | | 16 | 1 (6) |
| | | | Combination 1 + 2 | [5]Remove or Destroy genomic DNA | 12 | 1 (8) |

Note:
[1]Post treatment usually occurs after activation, preferable for 1 hour (or to 12 hours) but would stop prior to normal embryo cleavage and is provided to prevent intermingling of genomic and introduced DNA
[2]Fusion is preferred using described Electrical, Viral or PEG methods
[3]Activation is preferred using described chemical (Ethanol, Strontium Calcium Ionophore etc) or electrical methods
[4]Cell Injection/Insertion is insertion of new DNA (without fusion) using microinjection methods (piezo, microinjection) without destruction of the MI or MII plates
[5]Removal or destruction of the metaphase DNA is preferred using enucleation (micromanipulation/extraction, piezo etc) or by chemical or laser microsurgery methods. Removal is preferable before the first cleavage or to stop association of metaphase DNA to inserted/fused karyoplast DNA.

EXAMPLE 5

The effect of delaying activation in pig oocytes

TABLE 3

| Time delayed | No. of Oocytes | No. of Oocytes Fused (%) |
|---|---|---|
| 1 ñ 2 hrs | 131 | 57(43.5) |
| 4 ñ 6 hrs | 104 | 63(60.6) |

EXAMPLE 6

Efficiency of Transgenesis in Porcine Embryos Produced by Nuclear Transfer (NT) and Nuclear Addition (NA)

TABLE 4

| Group | Oocytes | Fused (%) | Cleaved (%) | Blastocysts (%) | Transgenic (%) |
|---|---|---|---|---|---|
| NT | 196 | 87(44.4) | 42(48.2) | 12(13.7) | 1(8.3) |
| NA | 210 | 101(48.1) | 50(79.2) | 26(25.7) | 3(11.5) |

The DNA construct used was pGalloway which is based on the porcine α1,3-galactosyltransferase gene

REFERENCES

1. Thomson J A, ltskovitz-Eldor J, Shapiro S S, Waknitz M A, Swiergiel J J, Marshall V S, Jones J M: Embryonic stem cell lines derived from human blastocysts. *Science* 1998, 282:1145-1147.
2. Reubinoff B E, Pera M F, Fong C Y, Trounson A O, Bongso A: Embryonic stem cell lines from human blastocysts: somatic differentiation in vitro. *Nature Biotechnology* 2000, 18:399-404.
3. Smith A G: Cell therapy: In search of pluripotency. *Current Biology* 1998, 8: R802-804.
4. Solter D: Dolly is a clone—and no longer alone. *Nature* 1998, 394: 315.
5. Wilmut I, Schnieke A E, McWhir J, Kind A J, Campbell K H: Viable offspring derived from fetal and adult mammalian cells. *Nature* 1997, 385:810-813.
6. Wakayama T, Perry A C, Zuccotti M, Johnson K R, Yanagimachi R: Full-term development of mice from enucleated oocytes injected with cumulus cell nuclei. *Nature* 1998, 394:369-374.
7. Mountford P M, Smith A G: Internal ribosome entry sites and dicistronic RNAs in mammalian transgenesis. *TIG* 1995, 11:179-184.
8. Munsie M, Peura T P, Michalska A, Trounson A O, Mountford P S: Novel method for demonstrating nuclear contribution in mouse nuclear transfer. *Reproduction Fertility and Development* 1998, 10:633-637.
9. Cibelli J B, Stice S L, Golueke P J, Kane J J, Jerry J, Blackwell C, Ponce de Leon F A, Robl J M: Transgenic bovine chimeric offspring produced from somatic cell-derived stem-like cells. *Nature Biotechnology* 1998, 16:642-646.
10. Klug M G, Soonpaa M H, Koh G Y, Field L J: Genetically selected cardiomyocytes from differentiating embryonic stem cells form stable intracardiac grafts. *Journal of Clinical Investigation* 1996, 98:216-224.
11. McDonald J W, Liu X-Z, Qu Y, Liu S, Mickey S K, Turetsky D, Gottlieb D I, Choi D W: Transplanted embryonic stem cells survive, differentiate and promote recovery in injured rat spinal cord. *Nature Medicine* 1999, 5: 1410-1412.
12. Potocnik A J, Kohler H, Eichmann K: Hemato-lymphoid in vivo reconstitution potential of subpopulations derived from in vitro differentiated embryonic stem cells. *Proc Natl Acad Sci USA* 1997, 94:10295-10300.
13. Soria B, Roche E, Berna G, Leon-Quinto T, Reig J A, Matrin F: Insulin-sectreting cells derived from embryonic stem cells normalize glycemia in streptozotocin-induced diabetic mice. *Diabetes* 2000, 49:157-162
14. Bames F L, Crombie A, Gardner D K, Kausche A, Lacham-Kaplan O, Suikkari A-M, Tiglias J. Wood C, Trounson A O: Blastocyst development and birth after in vitro maturation of human primary oocytes, intracytoplasmic sperm injection and assisted hatching. Hum Reprod 1995, 10:3243-3247.
15. Robertson E J: Teratocarcinomas and embryonic stem cells: A practical Approach. Oxford: IRL Press; 1987.
16. Smith A G: Culture and differentiation of embryonic stem cells. J Tiss Cult Meth 1991, 13:89-94.
17. Buehr M., McLaren A: Isolation and culture of primordial germ cells. Methods Enzymol 1993, 225:58-77.
18. van Eijk MJT, van Rooijen M A, Modina S, Scesi L, Folkers G, van Tol HTA, Bevers M M, Fisher S R, Lewin H A, Rakacolli D, Galli C, de Vaureix C, Trounson A O, Mummery C L, Gandolfi F: Molecular cloning, genetic mapping, and developmental expression of bovine POU5F1. Biol Reprod 1999, 60:1093-1103.
19. Agulnik A I, Longepied G, Ty M T, Bishop C E, Mitchell M: Mouse H-Y encoding Smcy gene and its X chromosomal homolog Smcx. Mamm Genome 1999, 10:926-929.
20. Nagy A, Rossant J, Nagy R, Abramow-Newerly W, Roder J C: Derivation of completely cell culture-derived mice from early-passage embryonic stem cells. Proc Natl Acad Sci USA 1993, 90:8424-8428.
21. Bradley A: Teratocarcinomas and embryonic stem cells: A practical approach. Oxford: IRL Press; 1987.
22. Li M, Pevny L, Lovell-Badge R, Smith A: Generation of purified neural precursors from embryonic stem cells by lineage selection. Curr Biol 1998, 8:971-974.
23. Doetschman T C, Eistetter H, Katz M, Schmidt W, Kemler R: The in vitro development of blastocyst-derived embryonic stem cell lines: formation of visceral yolk sac, blood islands and myocardium. J Embryol Exp Morphol 1985, 87:27-45.
24. Beddington R S P, Morgenstern J, Land H, Hogan A: An in situ transgenic enzyme marker for the midgestation mouse embryo and the visualization of inner cell mass clones during early embryogenesis. Development 1989, 106: 37-46.
25. Sambrook, J., Fritsch, E. F., Maniatis, T., (1989) Molecular Cloning—A Laboratory Manual, Cold Spring Harbour Laboratory Press, New York);
26 (O'Gorman, S., Fox, D. T., Wahl, G. M. (1991) Recombinase-mediated gene activation and site-specific integration in mammalian cells. Science 251(4999), 1351-5).

Finally, it is to be understood that various alterations, modifications and/or additions may be made without departing from the spirit of the present invention as outlined herein.

The invention claimed is:

1. A method of preparing a reprogrammed diploid mammalian cell comprising providing a diploid mammalian donor nucleus derived from a somatic cell, and a mammalian recipient cell, wherein the diploid mammalian donor nucleus and the mammalian recipient cell are of the same species;
   introducing the mammalian donor nucleus into the mammalian recipient cell to produce an aneuploid cell;
   maintaining the aneuploid cell in a suitable environment for a period sufficient to allow the donor nucleus to be reprogrammed;
   subjecting the aneuploid cell to an activation step; and
   subsequent to maintaining the aneuploid cell in the suitable environment, treating said reprogrammed aneuploid cell so as to generate a reprogrammed diploid mammalian cell from said reprogrammed aneuploid cell by removal or destruction of the mammalian recipient cell nucleus, pronucleus, metaphase plate, chromatin, chromosomes or nuclear DNA from said reprogrammed aneuploid cell.

2. A method according to claim 1, wherein the mammalian recipient cell is an oocyte, zygote, or embryonic blastomere.

3. A method according to claim 2, wherein the oocyte is a metaphase II oocyte.

4. A method according to claim 1, wherein the mammalian recipient cell is a pluripotent stem cell.

5. A method according to claim 4, wherein the mammalian recipient cell is an embryonic stem cell, embryonic germ cell, primordial germ cell, or embryonal carcinoma cell.

6. A method according to claim 1, wherein the mammalian donor nucleus is a nucleus derived from a cumulus cell.

7. A method according to claim 1, wherein the mammalian donor nucleus is transferred to the recipient cell by piezo-assisted micromanipulation.

8. A method according to claim 1, wherein nucleus or nuclear DNA of the mammalian recipient cell is removed or destroyed prior to division of the aneuploid cell.

9. A method according to claim 1, wherein the mammalian donor cell nucleus is reprogrammed to an embryonic cell nucleus.

10. A method according to claim 9, wherein the reprogrammed mammalian cell nucleus forms a mammalian embryo containing embryonic cells.

11. A method according to claim 1, wherein the mammalian recipient cell is a human cell.

12. A method according to claim 1, wherein the mammalian recipient cell is a mouse cell.

13. The method according to claim 1, wherein said treating comprises at least one of the group consisting of enucleation by micromanipulation, chemical microsurgery and laser microsurgery.

14. A method of preparing a reprogrammed genetically modified diploid mammalian cell comprising
providing a genetically modified diploid mammalian donor nucleus derived from a genetically modified somatic cell, and a mammalian recipient cell, wherein the genetically modified diploid mammalian donor nucleus and the mammalian recipient cell are of the same species;
introducing the genetically modified mammalian donor nucleus into the mammalian recipient cell to produce an aneuploid cell;
maintaining the aneuploid cell in a suitable environment for a period sufficient to allow the donor nucleus to be reprogrammed;
subjecting the aneuploid cell to an activation step; and
subsequent to maintaining the aneuploid cell in the suitable environment, treating said reprogrammed aneuploid cell so as to generate a reprogrammed genetically modified diploid mammalian cell from said reprogrammed aneuploid cell by removal or destruction of the mammalian recipient cell nucleus, pronucleus, metaphase plate, chromatin, chromosomes or nuclear DNA from said reprogrammed aneuploid cell.

15. A method of preparing a reprogrammed genetically abnormal diploid mammalian cell comprising
providing a genetically abnormal diploid mammalian donor nucleus derived from a genetically abnormal somatic cell comprising a mutation associated with a genetic disease, and a mammalian recipient cell, wherein the genetically abnormal diploid mammalian donor nucleus and the mammalian recipient cell are of the same species;
introducing the genetically abnormal mammalian donor nucleus into the mammalian recipient cell to produce an aneuploid cell;
maintaining the aneuploid cell in a suitable environment for a period sufficient to allow the donor nucleus to be reprogrammed;
subjecting the aneuploid cell to an activation step; and
subsequent to maintaining the aneuploid cell in the suitable environment, treating said reprogrammed aneuploid cell so as to generate a reprogrammed genetically abnormal diploid mammalian cell from said reprogrammed aneuploid cell by removal or destruction of the mammalian recipient cell nucleus, pronucleus, metaphase plate, chromatin, chromosomes or nuclear DNA from said reprogrammed aneuploid cell.

16. A method of generating one of a group consisting of a cell and cell line from a reprogrammed diploid mammalian cell, comprising:
(a) preparing a reprogrammed diploid mammalian cell by providing: providing a diploid mammalian donor nucleus derived from a somatic cell, and a mammalian recipient cell, wherein the diploid mammalian donor nucleus and the mammalian recipient cell are of the same species;
introducing the mammalian donor nucleus into the mammalian recipient cell to produce an aneuploid cell;
maintaining the aneuploid cell in a suitable environment for a period sufficient to allow the donor nucleus to be reprogrammed;
subjecting the aneuploid cell to an activation step; and
subsequent to maintaining the aneuploid cell in the suitable environment, treating said reprogrammed aneuploid cell so as to generate a reprogrammed diploid mammalian cell from said reprogrammed aneuploid cell by removal or destruction of the mammalian recipient cell nucleus, pronucleus, metaphase plate, chromatin, chromosomes or nuclear DNA from said reprogrammed aneuploid cell; and
(b) generating one of a group consisting of a cell and a cell line, from said reprogrammed diploid mammalian cell.

17. A method according to claim 16, wherein the one of a group consisting of a cell and a cell line, has been genetically modified to eliminate or reduce an undesirable activity or to provide or increase a desirable activity.

18. A method of preparing a reprogrammed mammalian cell comprising
providing a diploid mammalian donor nucleus derived from a somatic cell, an exogenous nucleic acid molecule and a mammalian recipient cell, wherein the genetically modified diploid mammalian donor nucleus and the mammalian recipient cell are of the same species;
introducing the mammalian donor nucleus and exogenous nucleic acid molecule into the mammalian recipient cell to produce an aneuploid cell;
maintaining the aneuploid cell in a suitable environment for a period sufficient to allow the donor nucleus to be reprogrammed;
subjecting the aneuploid cell to an activation step; and
subsequent to maintaining the aneuploid cell in the suitable environment, treating said reprogrammed aneuploid cell so as to generate a reprogrammed diploid mammalian cell comprising an exogenous nucleic acid sequence from said reprogrammed aneuploid cell by removal or destruction of the mammalian recipient cell nucleus, pronucleus, metaphase plate, chromatin, chromosomes or nuclear DNA from said reprogrammed aneuploid cell.

19. A method of preparing a reprogrammed diploid embryonic mammalian cell comprising:
providing a diploid mammalian donor nucleus derived from a somatic cell, and a mammalian recipient cell and one of a group consisting of a recipient mammalian oocyte and an embryonic cell, wherein the diploid mammalian donor nucleus and the mammalian recipient cell are of the same species;

introducing the mammalian donor cell nucleus into the mammalian recipient oocyte or embryonic cell to produce an aneuploid cell;

maintaining the aneuploid cell in a suitable environment for a period sufficient to allow the mammalian donor cell nucleus to be reprogrammed; and subjecting the aneuploid cell to an activation step;

subsequent to maintaining the aneuploid cell in the suitable environment, treating said reprogrammed aneuploid cell so as to generate a reprogrammed diploid embryonic mammalian cell from said reprogrammed aneuploid cell by removal or destruction of the mammalian recipient cell nucleus, pronucleus, metaphase plate, chromatin, chromosomes or nuclear DNA from said reprogrammed aneuploid cell or one or more of its daughter cells.

20. The method according to claim 19, wherein said treating comprises at least one of the group consisting of enucleation by micromanipulation, chemical microsurgery and laser microsurgery.

* * * * *